US008330952B2

United States Patent
Wu et al.

(10) Patent No.: US 8,330,952 B2
(45) Date of Patent: Dec. 11, 2012

(54) GUIDED MODE RESONATOR BASED RAMAN ENHANCEMENT APPARATUS

(75) Inventors: Wei Wu, Palo Alto, CA (US); Jingjing Li, Palo Alto, CA (US); Qiangfei Xia, Palo Alto, CA (US); Jianhua Yang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 475 days.

(21) Appl. No.: 12/625,304

(22) Filed: Nov. 24, 2009

(65) Prior Publication Data

US 2011/0122405 A1  May 26, 2011

(51) Int. Cl.
*G01J 3/44* (2006.01)
(52) U.S. Cl. ....................................................... 356/301
(58) Field of Classification Search .............. 356/72–73, 356/301
See application file for complete search history.

(56) References Cited

U.S. PATENT DOCUMENTS
6,785,433 B2 *  8/2004  Tiefenthaler ................... 385/12

* cited by examiner

*Primary Examiner* — Tarifur Chowdhury
*Assistant Examiner* — Abdullahi Nur
(74) *Attorney, Agent, or Firm* — David W. Collins (57) ABSTRACT

A system for performing Raman spectroscopy comprises a waveguide layer configured with at least one array of features, the at least one array of features being configured to provide guided-mode resonance for at least one wavelength of electromagnetic radiation; and at least one fluid channel disposed in the waveguide layer. An analyte sensor comprises an electromagnetic radiation source configured to emit a range of wavelengths of electromagnetic radiation, the system for performing Raman spectroscopy, and at least one photodetector configured to detect Raman scattered light.

20 Claims, 9 Drawing Sheets

GUIDED MODE RESONATOR BASED RAMAN ENHANCEMENT APPARATUS

STATEMENT OF GOVERNMENT INTEREST

This invention has been made with Government support under Contract No. HR0011-09-3-0002, awarded by the Defense Advanced Research Projects Agency. The government has certain rights in the invention.

TECHNICAL FIELD

Embodiments of the present invention relate generally to systems for performing surface-enhanced Raman spectroscopy (SERS).

BACKGROUND ART

Raman spectroscopy is a spectroscopic technique used in condensed matter physics and chemistry to study vibrational, rotational, and other low-frequency modes in molecular systems. In a Raman spectroscopic experiment, an approximately monochromatic beam of light of a particular wavelength range passes through a sample of molecules and a spectrum of scattered light is emitted. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Raman spectrums that can be used like a fingerprint to identify molecules and even determine the structure of molecules.

The Raman scattered light generated by a compound (or ion) adsorbed on or within a few nanometers of a structured metal surface can be $10^3$-$10^{14}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

However, most SERS systems only enhance the electromagnetic field at certain hot spots. They have substantial enhancement factors at those hot spots, but most Raman measurements see the integrated effects over certain area. That makes those systems based on hot spots less effective.

BEST MODES FOR CARRYING OUT THE INVENTION

Reference is made now in detail to specific embodiments, which illustrates the best mode presently contemplated by the inventors for practicing the invention. Alternative embodiments are also briefly described as applicable.

Embodiments of the present invention are directed to systems for performing surface-enhanced Raman spectroscopy. The systems include a waveguide configured with an array of features to support guided-mode resonance for certain wavelengths of Raman-excitation light which increases the intensity of the electromagnetic field associated with the Raman-excitation light. In particular, wavelengths of the Raman-excitation light can be selected to generate a spectrum of Raman scattered light associated with particular analyte molecules, and the waveguide and array of features can be configured to provide guided-mode resonance for the Raman-excitation light. Portions of the outer surfaces of the array of features are coated with a Raman-active material that when exposed to the Raman-excitation light cause analyte molecules located on, or in close proximity to, the Raman-active material to enhance the intensity of the Raman-scattered light.

The term "light" as used to describe the operation of system embodiments of the present invention is not intended to be limited to electromagnetic radiation with wavelengths that lie only within the visible portion of the electromagnetic spectrum, but is intended to also include electromagnetic radiation with wavelengths outside the visible portion, such as the infrared and ultraviolet portions of the electromagnetic spectrum, and can be used to refer to both classical and quantum electromagnetic radiation.

Further, as used herein, the article 'a' is intended to have its ordinary meaning in the patent arts, namely 'one or more'. For example, "a fluid channel" means one or more fluid channels and as such, "the fluid channel" explicitly means "the fluid channel(s)" herein. Also, any reference herein to 'top', 'bottom', 'upper', 'lower', 'up', 'down', 'front', 'back', 'left' or 'right' is not intended to be a limitation herein. Herein, the term 'about' when applied to a value generally means plus or minus 10% unless otherwise expressly specified. Moreover, examples herein are intended to be illustrative only and are presented for discussion purposes and not by way of limitation.

In accordance with the teachings herein, at least one fluid channel is embedded in the waveguide layer of a guided mode resonator (GMR). The chemical/molecules flow through the channel(s) and they are located at the maximum of the electromagnetic field E. $E^2$ is enhanced by Q of the GMR, therefore the Raman enhancement will be $Q^2$. Q can be larger than 1 million easily and the electromagnetic field enhancement is not limited to hot spots. The enhancement factor $Q=E_{excitation}^2 \times E_{signal}^2$. The guided mode resonator enhances the Raman signal. The Raman signal is enhanced by $Q^2$ substantially almost uniformly across the entire apparatus, instead of just on the hot spots like most SERS systems. Each resonant mode has an optical field distribution, so the enhancement is not exactly uniform. But comparing with the SERS system with hot spots, the present system is very uniform.

Figure 1A:
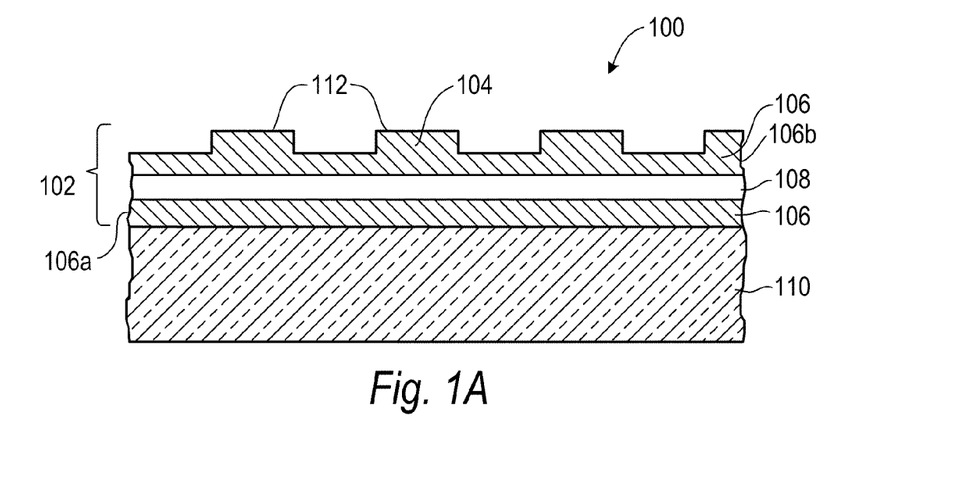
FIG. 1A depicts a cross-sectional view of a Raman-active system, according to an embodiment of the present invention.

FIG. 1A illustrates an embodiment of a SERS, or Raman, system 100 that uses guided-mode resonance (GMR). The SERS system 100 includes a guided-mode resonator 102 comprising a grating layer 104 formed in a waveguide layer 106. A fluid channel 108 is embedded in the waveguide layer 106. In the embodiment shown in FIG. 1A, the fluid channel 108 lies beneath the grating layer 104 and runs perpendicular to it (see, e.g., FIG. 1B). The GMR 102 may be supported on a substrate 110.

As is well-known, a GMR grating typically consists of a planar dielectric waveguide and a subwavelength periodic array of lines, protrusions or holes.

When the spatial period of the grating matches the propagating wavelength of a guided mode, strong resonant features are shown in the transmission and/or reflection. An enhanced optical field also builds up within the waveguide layer and the space adjacent to the waveguide layer (some modes extend more to outside and some less depending on the design).

A cover layer (not shown) may optionally be formed on top of the grating layer 104. The cover layer is a protective layer and can be made of a material such as silicon dioxide but may additionally include an antireflective coating to prevent reflection at a top surface of the SERS system 100, a bandpass optical filter to select the wavelength of light reaching grating layer 104, or any other optical coating.

Grating layer 104/waveguide layer 106 comprises a material having a refractive index that is higher than the refractive index of a fluid flowing through the fluid channel 108. Grating layer 104/waveguide layer 106 may comprise, for example, silicon nitride ($Si_3N_4$) or silicon-rich silicon nitride (referred to as $SiN_x$, where x is in the range of 0.5 to 2). Other materials include, but are not limited to, Si, $Al_2O_3$, $TiO_x$, InP, GaAs, $In_xGa_{1-x}As_yP_{1-y}$, etc. In this connection, it will be noted that the fluid, which is discussed in greater detail below, typically has a refractive index of about 1.33 if the analyte is in water or about 1.5 if the analyte is in an organic solvent or about 1 if the analyte is in a gas.

Grating layer 104 has a pattern of features 112 that creates a resonance that strongly couples incident light (see FIGS. 10A-10C) into the fluid channel 108 only if the wavelength λ and direction of incident light satisfy specific conditions. In particular, with the wavelength of an alignment beam being known and fixed, grating layer 104 can be patterned so that resonant coupling only occurs if the incident alignment beam has (or is close to) a specific incident direction. The specific design of grating layer 104 will depend on the wavelength λ and incident direction of light to be detected and may be produced using GMR filter design techniques that are known in the art. By "specific design" is meant the width (w) and height (h) of the features 112 and their periodicity (a) (shown in FIG. 1B).

Figure 1B:
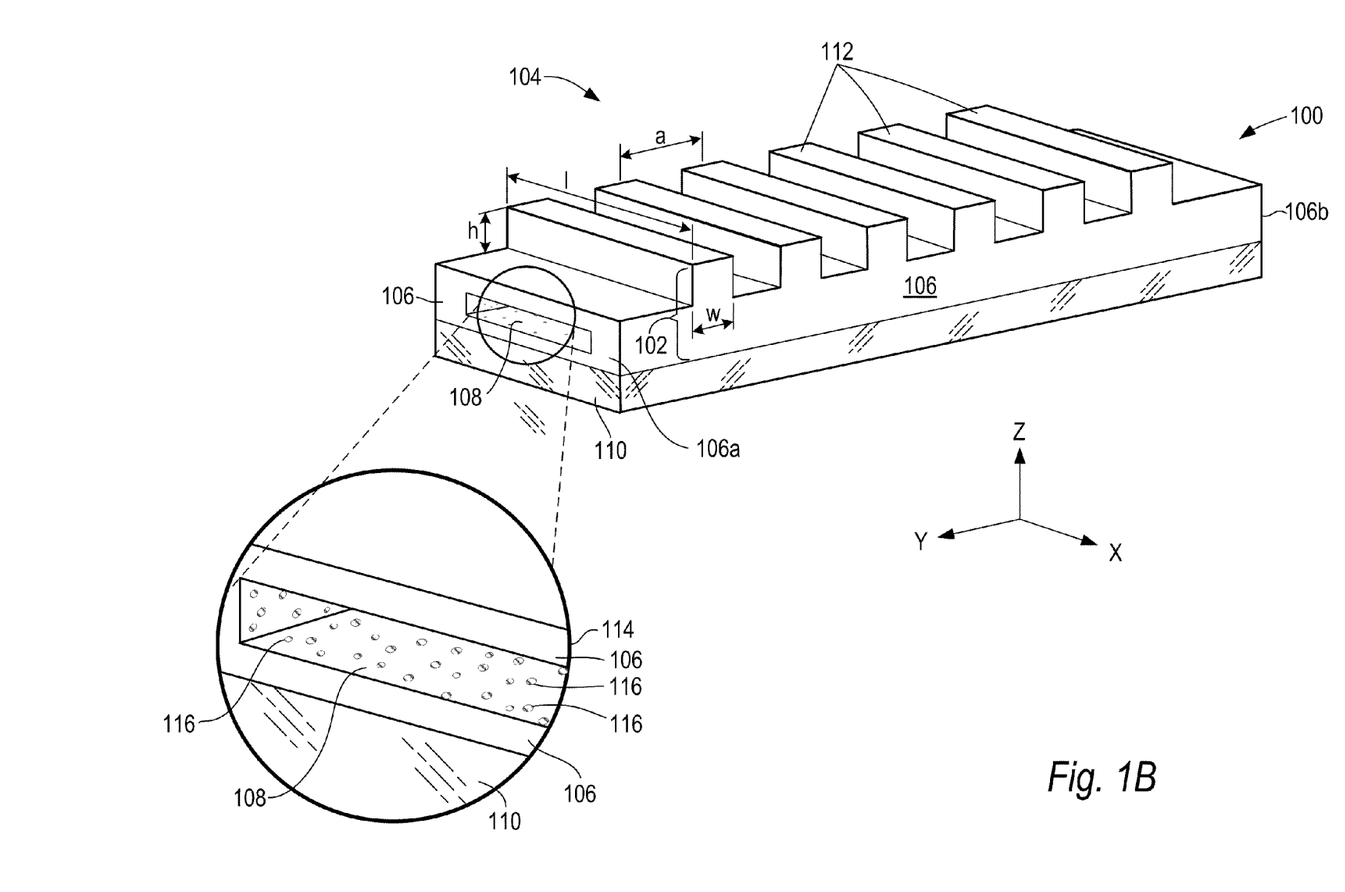
FIGS. 1B and 2-7 show isometric views of six different Raman-active systems, each system configured with a different array of features in accordance with embodiments of the present invention.

FIG. 1B shows an isometric view of the Raman-active system 100 shown in FIG. 1A and configured in accordance with embodiments of the present invention. As discussed above, the Raman-active system 100 includes the grating layer 104/waveguide layer 106. The grating layer 104 includes the array of features 112 protruding from the waveguide layer 106 and formed from the same material comprising the waveguide layer. The features 112 are approximately regularly-spaced with rectangular-shaped cross-sections. The features 112 form a one-dimensional lattice above the waveguide layer 106 with an approximately constant lattice spacing a in the Y-direction. As shown in the example of FIG. 1B, the length l of the features 112 substantially matches the width of the waveguide layer 106, and the height h and width w of each feature 112 and lattice constant a can be selected to support guided-mode resonance for wavelengths of Raman-excitation light injected into the waveguide layer 106.

The fluid channel 108 extends from one end 106a of the waveguide layer 106 to the other end 106b, and appropriate inlet and outlet devices, including valves, recirculators, and the like (not shown), may be used to introduce fluid (liquid or gas) containing the analyte to be analyzed into one end of the fluid channel, remove the fluid from the other end, and recirculate it as desired.

In certain embodiments, the waveguide layer 102 can be disposed on a surface of a substrate 110. The substrate 110 can comprise a material having a lower refractive index than the waveguide layer material and serve as a cladding layer for the waveguide layer 106. In other embodiments, the substrate 110 can be eliminated with an air cladding surrounding the waveguide layer 106 and the features 112. The substrate 110 may be optically opaque or optically transparent, depending on the use of the Raman system 100.

The combination of the grating layer 104 and the fluid channel 108 results in an enhanced Raman signal. However, the enhancement can be further improved by coating the inside surfaces of the fluid channel 108 with a Raman-active material. Thus, in certain embodiments, the inner surfaces (top, bottom, sides) of the fluid channel 108 may be coated with a Raman-active material in the form of Raman-active nanoparticles. In the example of FIG. 1B, a portion of the fluid channel 108 is magnified in an enlargement 114 revealing Raman-active nanoparticles 116 disposed on the inside surfaces of the fluid channel 108. In other embodiments, the Raman-active material may be deposited as a thin Raman-active layer coating at least a portion of the inner surfaces of the fluid channel 108. The disposition of the Raman-active nanoparticles 116 and the deposition of a thin Raman-active layer are well-known. Examples of such Raman-active materials include gold, silver, copper, alloys thereof, or another suitable metal for forming surface plasmon polaritons or localized surface plasmon when illuminated by the electromagnetic radiation.

Figure 2:
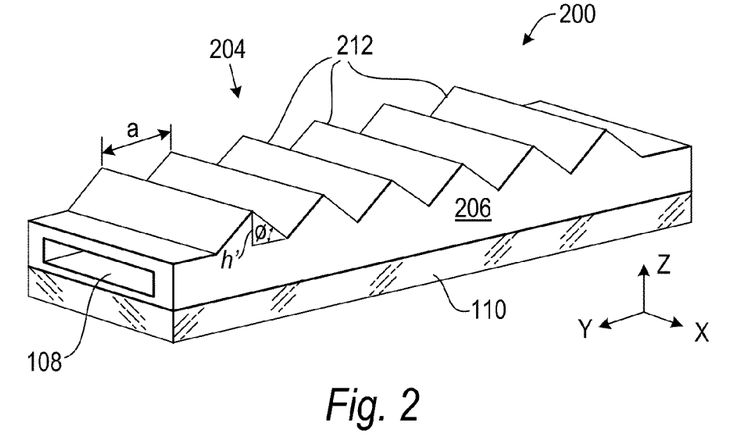

FIG. 2 shows an isometric view of a Raman-active system 200 configured in accordance with embodiments of the present invention. The Raman-active system 200 is nearly identical to the Raman-active system 100. In particular, the Raman-active system 200 includes the same grating layer 104/waveguide layer 106, here denoted 204/206, but the array of features instead comprises approximately regularly-spaced, saw-tooth-shaped features 212 protruding from the waveguide layer 206. The saw-tooth-shaped features 212 have a height h' and a slope angle φ relative to the normal. The features 212 also form a one-dimensional lattice above the waveguide layer 206 with an approximately constant lattice spacing a in the Y-direction. Although magnification of the fluid channel 108 is not shown in FIG. 2, in certain embodiments, the inner surfaces of the fluid channel may be coated with a Raman-active material in the form of Raman-active nanoparticles, as described above with reference to the Raman-active system 100. In other embodiments, the Raman-active material may be deposited as a thin Raman-active layer coating the inner surfaces of the fluid channel 108.

Figure 3:
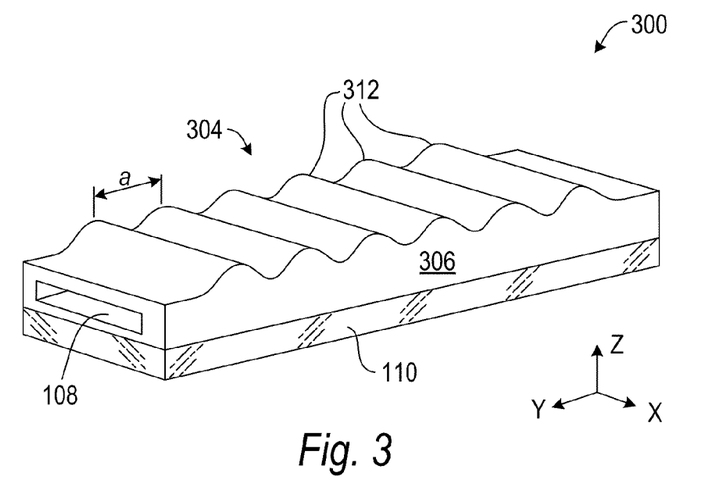

FIG. 3 shows an isometric view of a Raman-active system 300 configured in accordance with embodiments of the present invention. The Raman-active system 300 is also nearly identical to the Raman-active system 100. In particular, the Raman-active system 300 includes the same grating layer 104/waveguide layer 106, here denoted 304/306, but the array of features instead comprises a one-dimensional sinusoidal, or wave-like, pattern of alternating troughs and ridges protruding from the waveguide layer 306 and repeating in the Y-direction with an approximately constant lattice spacing a.

Although magnification of the fluid channel 108 is not provided in FIG. 3, in certain embodiments, the inner surfaces of the fluid channel may be coated with a Raman-active material in the form of Raman-active nanoparticles, as described above with reference to the Raman-active system 100. In other embodiments, the Raman-active material may be deposited as a thin Raman-active layer coating the inner surfaces of the fluid channel 108.

Embodiments of the present invention are not limited to one-dimensional arrays of features with between five and six features. The one-dimensional arrays of features can be composed of any suitable number of features protruding from the waveguide layer and extending in the Y-direction. Further, embodiments of the present invention are not limited to the one-dimensional (1-D) array configurations described above with reference to FIGS. 1-3. In other embodiments, the array pattern can also be extended into the X-direction to form a two-dimensional (2-D) array of features.

Figure 4:
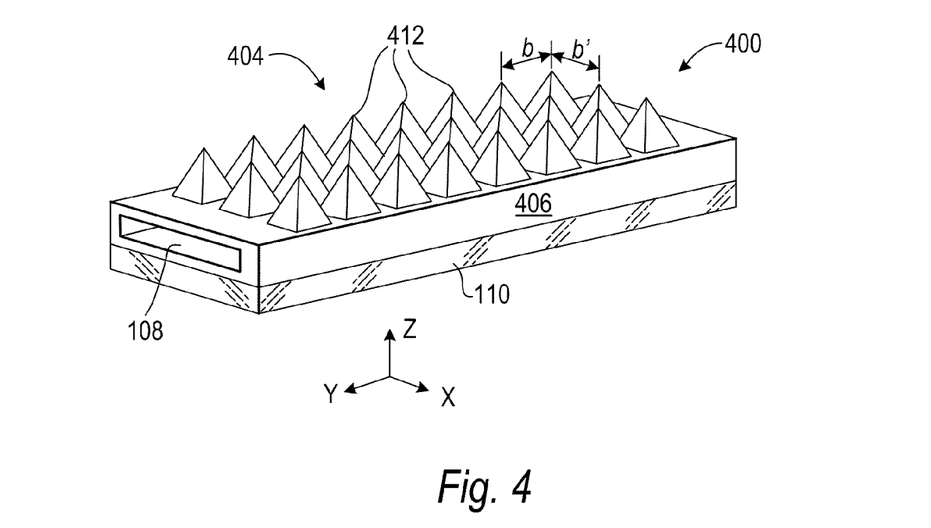

FIG. 4 shows an isometric view of a Raman-active system 400 configured in accordance with embodiments of the present invention. The Raman-active system 400 includes a waveguide layer 406 and an array of features 412 protruding from the waveguide layer and formed from waveguide layer material. The array of features 412 comprises approximately regularly-spaced, pyramid-shaped features 412. The features 412 form a two-dimensional array 404 protruding from the waveguide layer 406 with an approximately constant lattice spacing b in the Y-direction and an approximately constant lattice spacing b' in the X-direction. The lattice constants b and b' and height and base dimensions of the features 412 can be selected to support guided-mode resonance for various Raman-excitation light wavelengths.

As in the one-dimensional embodiments, although magnification of the fluid channel 108 is not provided in FIG. 4, in certain embodiments, the inner surfaces of the fluid channel 108 may be coated with a Raman-active material in the form of Raman-active nanoparticles, as described above with reference to the Raman-active system 100. In other embodiments, the Raman-active material may be deposited as a thin Raman-active layer coating at least a portion of the inner surfaces of the fluid channel 108.

In certain embodiments, as shown in FIG. 4, the waveguide layer 406 may be disposed on a surface of a substrate 110. The substrate 110 may comprise a material having a lower refractive index than the waveguide layer material and serve as a cladding layer for the waveguide layer 406. In other embodiments, the substrate 110 can be eliminated with an air cladding surrounding the waveguide layer 406 and the features 412.

Figure 5:
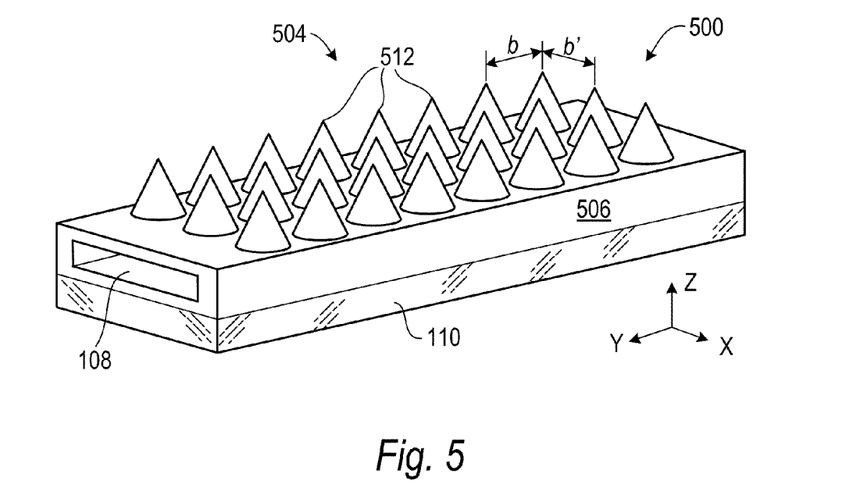

In other embodiments, the pyramid-shaped features of the Raman-active system 400 may be replaced by cone-shaped features. FIG. 5 shows an isometric view of a Raman-active system 500 configured in accordance with embodiments of the present invention. The Raman-active system 500 is nearly identical to the Raman-active system 400 except the array of features 512 of the Raman-active system 500 comprises a two-dimensional array 504 of cone-shaped features 512 protruding from the waveguide layer with an approximately constant lattice spacing b in the Y-direction and an approximately constant lattice spacing b' in the X-direction. Although magnification of the fluid channel 108 is not provided in FIG. 5, in certain embodiments, the inner surfaces of the fluid channel 108 may be coated with a Raman-active material in the form of Raman-active nanoparticles, as described above with reference to the Raman-active system 100. In other embodiments, the Raman-active material may be deposited as a thin Raman-active layer coating at least a portion of the inner surfaces of the fluid channel 108.

Figure 6:
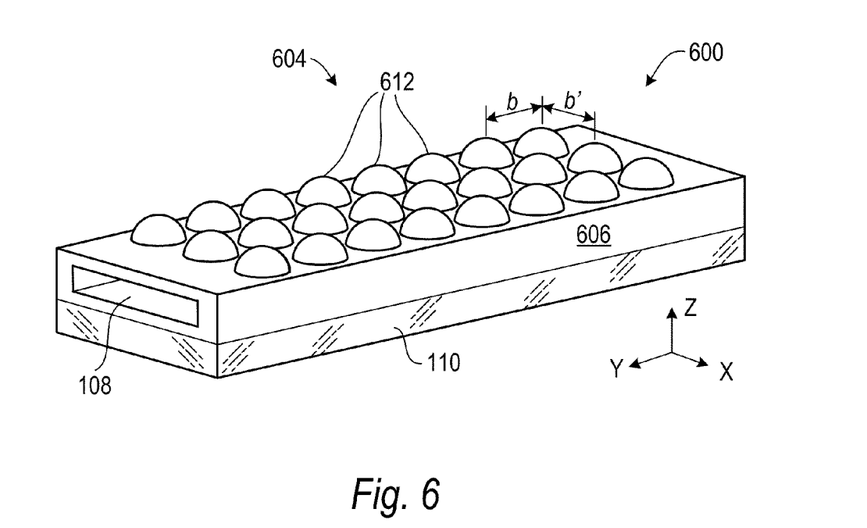

In other embodiments, the pyramid-shaped features of the Raman-active system 400 may be replaced by hemispherical-shaped features. FIG. 6 shows an isometric view of a Raman-active system 600 configured in accordance with embodiments of the present invention. The Raman-active system 600 is nearly identical to the Raman-active system 400 except the array of features 612 of the Raman-active system 600 is composed of a two-dimensional array 604 of hemispherical-shaped features 612 protruding from the waveguide layer with an approximately constant lattice spacing b in the Y-direction and an approximately constant lattice spacing b' in the X-direction. Although magnification of the fluid channel 108 is not provided in FIG. 6, in certain embodiments, the inner surfaces of the fluid channel 108 may be coated with a Raman-active material in the form of Raman-active nanoparticles, as described above with reference to the Raman-active system 100. In other embodiments, the Raman-active material may be deposited as a thin Raman-active layer coating at least a portion of the inner surfaces of the fluid channel 108.

Figure 7:
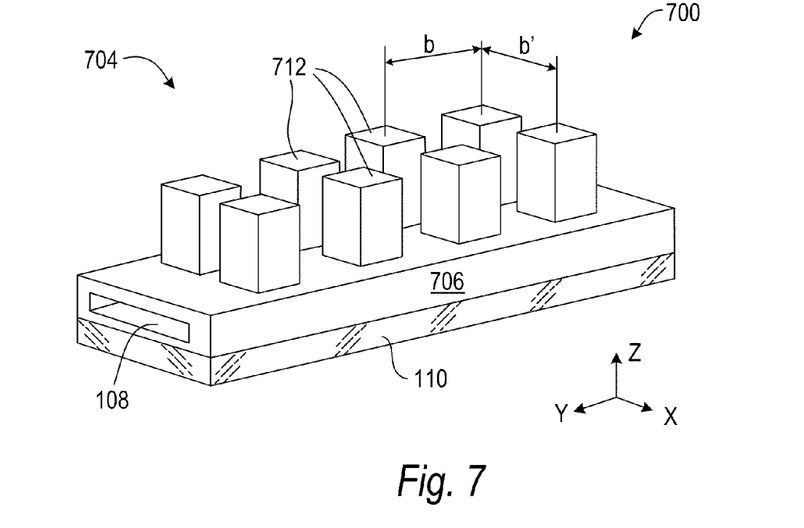

In other embodiments, the pyramid-shaped features of the Raman-active system 400 may be replaced by cuboid-shaped features. FIG. 7 shows an isometric view of a Raman-active system 700 configured in accordance with embodiments of the present invention. The Raman-active system 700 includes a waveguide layer 706 and an array of features 712 protruding from the waveguide layer and formed from waveguide layer material. The array of features 712 comprises approximately regularly-spaced, cuboid-shaped features 712. The features 712 form a two-dimensional array 704 protruding from the waveguide layer 406 with an approximately constant lattice spacing b in the Y-direction and an approximately constant lattice spacing b' in the X-direction. The lattice constants b and b' and height and base dimensions of the features 712 can be selected to support guided-mode resonance for various Raman-excitation light wavelengths. The shape may be cuboid (or rectangular prism) as shown in FIG. 7 or may be a square prism where at least two of the lengths (height and base) are the same or may be a cube, where all three lengths (height and base) are equal.

As in the one-dimensional embodiments, although magnification of the fluid channel 108 is not provided in FIG. 7, in certain embodiments, the inner surfaces of the fluid channel 108 may be coated with a Raman-active material in the form of Raman-active nanoparticles, as described above with reference to the Raman-active system 100. In other embodiments, the Raman-active material may be deposited as a thin Raman-active layer coating at least a portion of the inner surfaces of the fluid channel 108.

Embodiments of the present invention are not limited to three rows of features extending in the Y-direction along the length of the waveguide layer. In other embodiments, the number of rows extending along the length of the waveguide layer can range from as few as one row to two, four, or more rows of features. The number of features in each row of features extending in the X-direction can range from two to any suitable number of features. In other embodiments, the features forming a two-dimensional array of features can be configured with rectangular, square, cylindrical, elliptical, or any other suitably shaped XY-plane cross-section.

In all Figures, the fluid channel 108 is seen to be disposed perpendicular to the arrangement of the features 112, 212, 312, 412, 512, 612, 712.

Figure 8A:
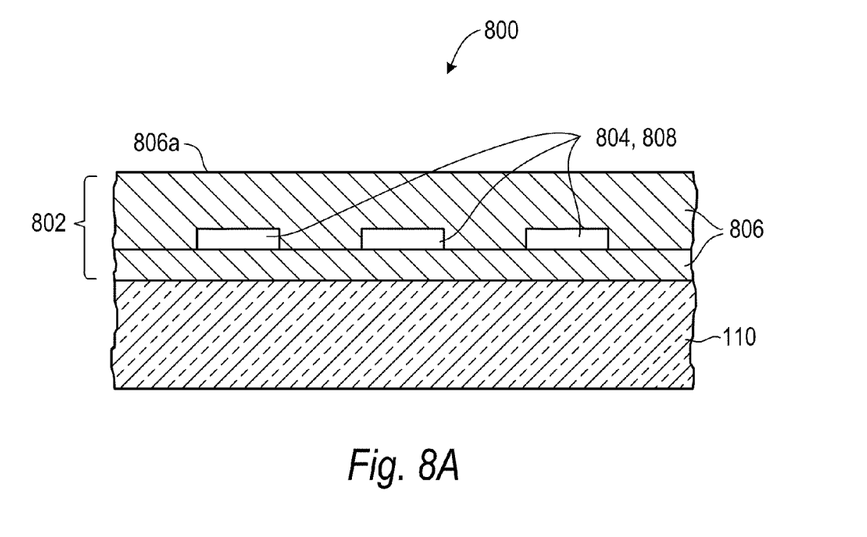
FIG. 8A depicts a cross-sectional view of another Raman-active system, according to an embodiment of the present invention.
Figure 8B:
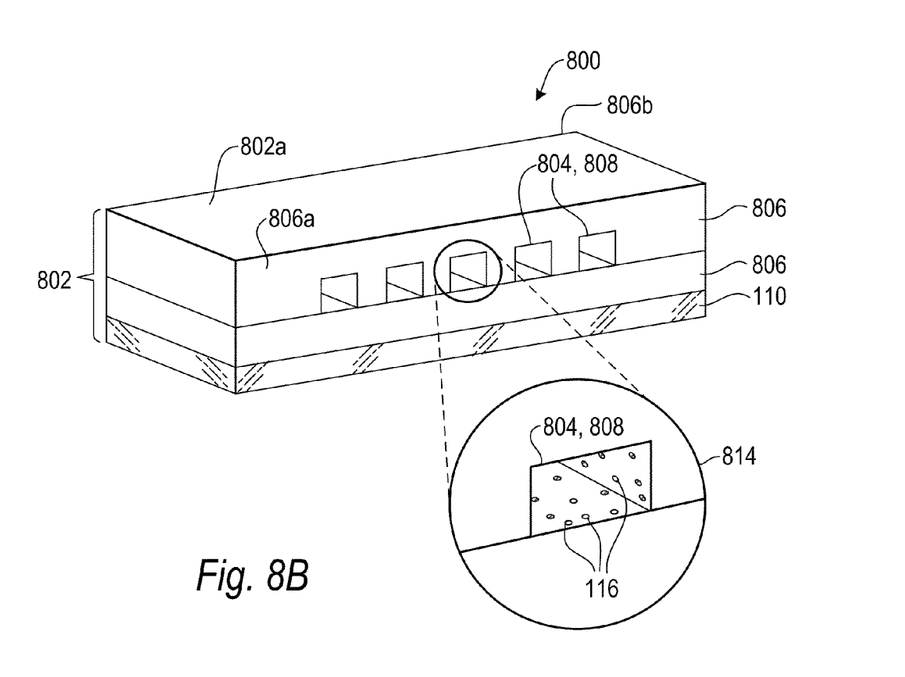
FIG. 8B depicts an isometric view of the Raman-active system of FIG. 8A.

FIGS. 8A-8B illustrate another embodiment of a SERS system 800 that also uses guided-mode resonance (GMR). The SERS system 800 includes a guided-mode resonator 802 comprising a grating layer 804 and a waveguide layer 806. A plurality of fluid channels 808 is embedded in the waveguide layer 806. The GMR 802 may be supported on substrate 110. In this case, the fluid channels 808 are dimensioned to also serve as the grating layer 804, and the same considerations described above with regard to grating layer 104 in FIGS. 1A-1B obtain here as well. In this embodiment, the top surface 802a of the guided-mode resonator 802 is seen to be featureless, since the grating 804 and fluid channels 808 are combined.

The combination of the grating layer 804 and the fluid channel 808 results in an enhanced Raman signal. However, the enhancement may be further improved by coating the inside surfaces of the fluid channel 808 with a Raman-active material. Thus, in certain embodiments, the inner surfaces (top, bottom, sides) of the fluid channel 808 may be coated with a Raman-active material in the form of Raman-active nanoparticles. In the example of FIG. 8B, a portion of the fluid channel 808 is magnified in an enlargement 814 revealing Raman-active nanoparticles 116 disposed on the inside surfaces of the fluid channel 808. In other embodiments, the Raman-active material may be deposited as a thin Raman-active layer coating at least a portion of the inner surfaces of the fluid channel 808. The disposition of the Raman-active nanoparticles 116 and the deposition of a thin Raman-active layer are well-known.

The fluid channel 808 extends from one end 806a of the waveguide layer 806 to the other end 806b, and appropriate inlet and outlet devices, including valves, recirculators, and the like (not shown), may be used to introduce fluid (liquid or gas) containing the analyte to be analyzed into one end of the fluid channel, remove the fluid from the other end, and recirculate it as desired.

The fluid flowing through the fluid channel(s) 108, 808 may be a gas or a liquid, in which the analyte of interest is entrained. If a gas is employed, the gas may be inert, such as nitrogen, helium, argon, or the like. In some embodiments, the gas may be air; this would be useful, for example, for detection of explosive components in air, such as airport security. If a liquid is employed, the liquid may comprise water or an organic solvent, such as ethanol, toluene, heptane, etc. In either case, the concentration of the analyte in the fluid may range from about 1 femtoMole to 1 mMole, or about 0.01 ppb to $10^4$ ppm.

Although the grating 804 in FIGS. 8A-8B is shown as rectangular in cross-section, the grating may alternatively be square in cross-section. Further, the cross-section of the grating may be saw-tooth-shaped as in FIG. 2 or sinusoidal (alternating ridges and trough) as in FIG. 3. The two-dimensional embodiments depicted in FIGS. 4-7 may also be employed as buried gratings, so long as the two-dimensional patterns (pyramidal, cone-shape, hemispherical-shape or cuboid) are connected to form fluidic channels.

Figure 9:
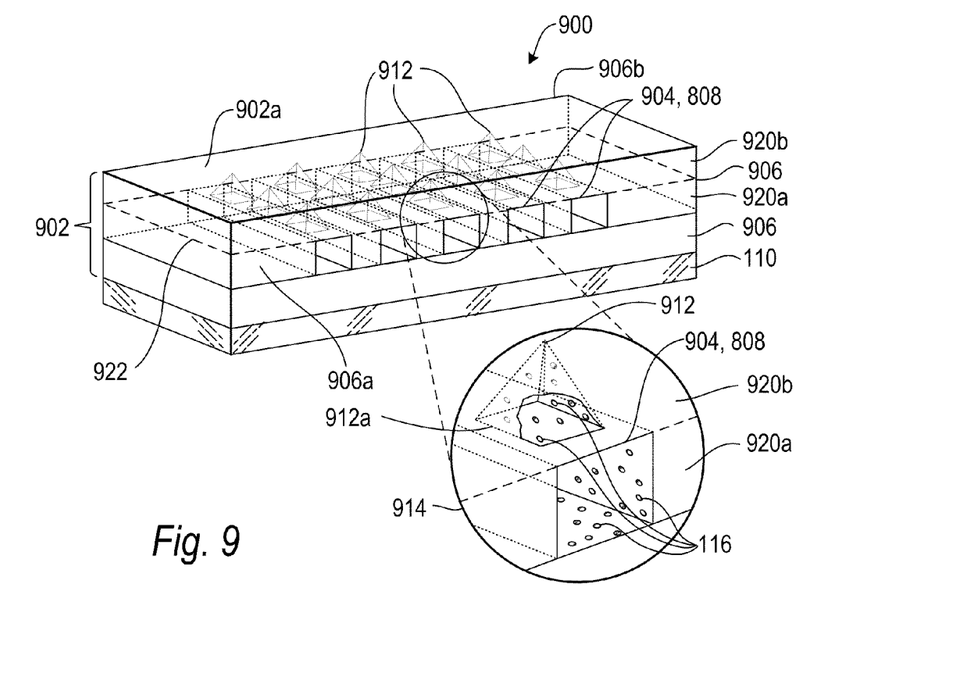
FIG. 9 depicts an isometric view of another Raman-active system, according to an embodiment of the present invention.

FIG. 9 shows an isometric view of a Raman-active system 900 configured in accordance with embodiments of the present invention. The Raman-active system 900 is an example of the Raman-active system 800 discussed above, having pyramidal features 912 arranged in a two-dimensional array.

The SERS system 900 includes a guided-mode resonator 902 comprising a grating layer 904 and a waveguide layer 906. A plurality of fluid channels 808 is embedded in the waveguide layer 906. The GMR 902 may be supported on substrate 110. In this case, the fluid channels 808 are dimensioned to also serve as the grating layer 904, and the same considerations described above with regard to combined grating layer 804/fluid channels 808 in FIGS. 8A-8B obtain here as well. In this embodiment, the top surface 902a of the guided-mode resonator 902 is seen to be featureless, since the grating 904 and fluid channels 808 are combined.

The combination of the grating layer 904 and the fluid channel 808 results in an enhanced Raman signal. However, the enhancement may be further improved by coating the inside surfaces of the fluid channel 808 with a Raman-active material. Thus, in certain embodiments, the inner surfaces (top, bottom, sides) of the fluid channel 808 may be coated with a Raman-active material in the form of Raman-active nanoparticles. In the example of FIG. 9, a portion of the fluid channel 808 is magnified in an enlargement 914 revealing Raman-active nanoparticles 116 disposed on the inside surfaces of the fluid channel 808. In other embodiments, the Raman-active material may be deposited as a thin Raman-active layer coating at least a portion of the inner surfaces of the fluid channel 808. The disposition of the Raman-active nanoparticles 116 and the deposition of a thin Raman-active layer are well-known.

The bases 912a of the pyramids are open to the channel 808 and are in fluid communication therewith. The inside surfaces of the pyramids 912, being exposed to the fluid flowing through the fluid channel 808, may also be coated with the Raman-active particles 116 or the Raman-active layer.

In certain embodiments, as shown in FIG. 9, the waveguide layer 906 may be disposed on a surface of a substrate 110. The substrate 110 may comprise a material having a lower refractive index than the waveguide layer material and serve as a cladding layer for the waveguide layer 906. In other embodiments, the substrate 110 can be eliminated with an air cladding surrounding the waveguide layer 906 and the features 912.

In a likewise fashion, other interior features such as cone-shape, hemispherical-shape or cuboid, as described above, may be utilized in conjunction with the fluid channels 808. The formation of such interior features may be accomplished in a number of ways. In one example, the channels 808 may be formed in one layer 920a and the features (pyramidal, cone-shape, hemispherical-shape or cuboid, etc.) may be formed in another layer 920b. The two layers may then be adhered together to match up the features and the channels, shown by the dashed line 922.

The Raman-active systems described above with reference to FIGS. 1-9 can be implemented in analyte sensors that are used to identify one or more analyte molecules by configuring the waveguide layer with an array of features that supports guided-mode resonance of appropriate wavelengths of the Raman-excitation light selected to stimulate emission of Raman scattered light from analyte molecules flowing through the fluid channel 108, which is located in close proximity to the features 112, 212, 312, 412, 512, 612, 712 or flowing through the fluid channels 808, which themselves form the grating 804, 904.

The Raman-active material disposed on the inner surfaces of the channel(s) 108, 808 further intensifies the Raman scattered light when illuminated by appropriate Raman excitation wavelengths. In either case, the Raman scattered light can be detected to produce a Raman spectrum that can be used like a finger print to identify the analyte.

Figure 10A:
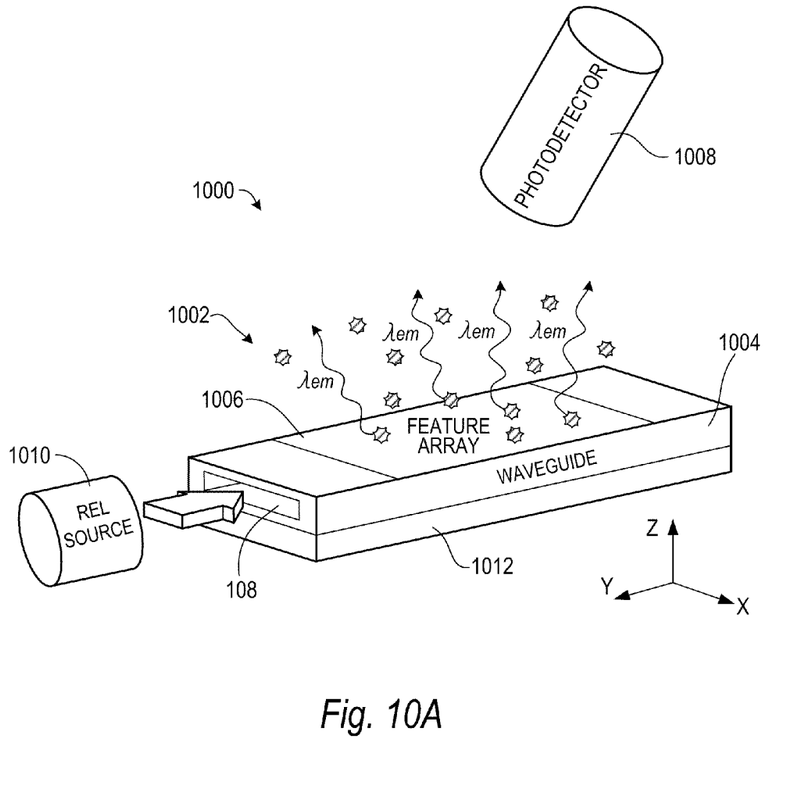
FIGS. 10A-10C each depict a schematic view of a sensing apparatus, according to embodiments of the present invention.
Figure 10B:
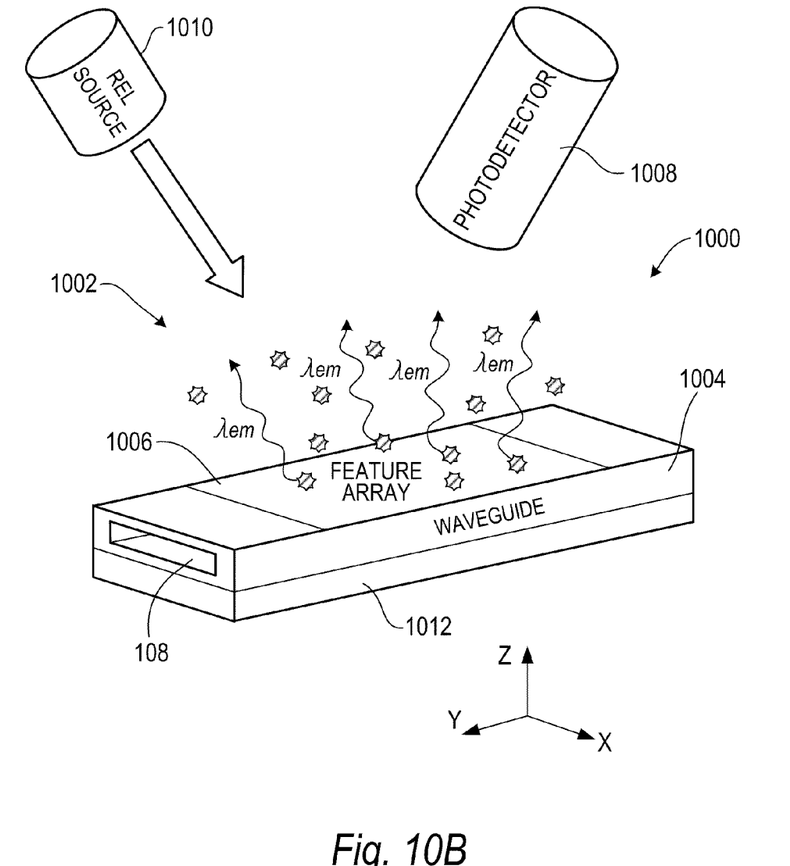
Figure 10C:
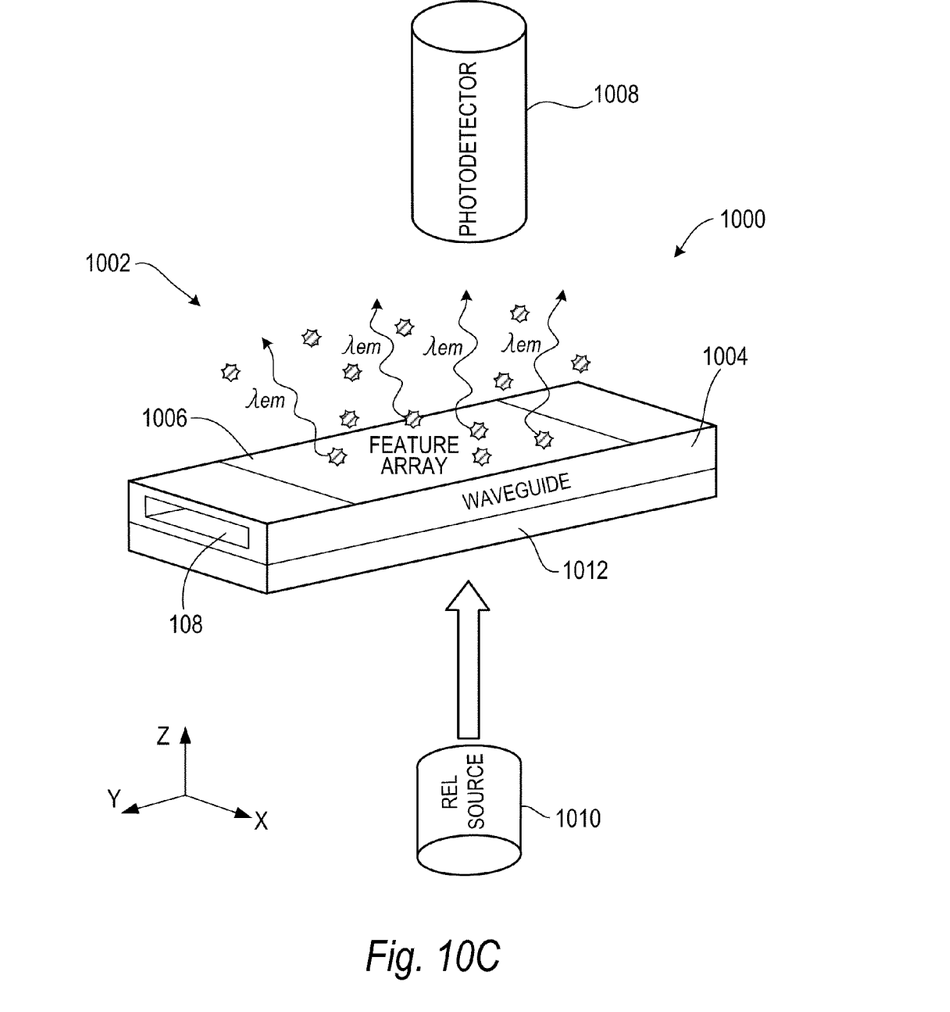

FIGS. 10A-10C show schematic representations of analyte sensors configured and operated in accordance with embodiments of the present invention. Analyte sensor 1000 includes a Raman-active system 1002 composed of a waveguide layer 1004 and an array of features 1006, as described above with reference to FIGS. 1-9, a photodetector 1008, and a Raman-excitation light source 1010. The Raman-active system 1000 includes a substrate 1012 that serves as a cladding layer, but in other embodiments, the waveguide layer 1004 can be configured with an air cladding region, as described above. In the example shown in FIG. 10A, the light source 1010 injects Raman-excitation light $\lambda_{em}$ into the waveguide layer 1004.

In the example shown in FIG. 10B, the light source 1010 is positioned so that Raman-excitation light is incident directly on the array of features 1006, rather than injecting the Raman-excitation light into the waveguide layer 1004.

In the example shown in FIG. 10C, the light source 1010 is positioned beneath the Raman-active system 1002 so that the Raman-excitation light passes through the substrate 1012 (if present) and the waveguide 1004 with its fluid channel 108. In this embodiment, the substrate 1012 (if present) is transparent to the incident light from the source 1010. In all three cases, the photodetector 1008 is positioned to capture at least a portion of the Raman scattered light emitted by an analyte in the fluid flowing through the fluid channel 108.

The array of features 1006 is configured to support guided-mode resonance with certain wavelengths of Raman-excitation light. Guided-mode resonance enhances, or increases, the intensity of the associated electromagnetic field. For example, when the wavelength of Raman-excitation light is resonant with an array of features, the electromagnetic field associated with the Raman-excitation light builds or is enhanced by guided-mode resonance within the waveguide. As a result, Raman-excitation light can be emitted or coupled out through the features and waveguide to interact with analyte molecules and cause emission of Raman scattered light from the analyte molecules located in the fluid channel 108. The enhanced electromagnetic field also interacts with the Raman-active material to further enhance this emission process for analyte molecules located on, or in close proximity to, the Raman-active material.

While FIGS. 10A-10C specifically show the Raman-active systems 100, 200, 300, 400, 500, 600, 700 of FIGS. 1-7 (fluid channel 108 beneath the features 112, 212, 312, 412, 512, 612, 712), it will be readily apparent that the Raman-active system may be replaced by the Raman-active systems 800, 900 of FIGS. 8-9. The same arrangements of source 1010 and detector 1008 depicted in FIGS. 10A-10C obtain in this case as well.

In operation, an analyte is introduced into the fluid channel (s) 108, 808 and Raman-excitation light of a suitable wavelength for establishing guided-mode resonance and for generating Raman scattered light from the analyte is injected into the waveguide layer 1004. As a result, the intensity of the electro-magnetic field associated with the Raman-excitation light increases, and the Raman-excitation light is output from the features 1006. The wavelengths selected for the Raman-excitation light cause the analyte located near the features 1006 and in the waveguide layer 1004 to emit a Raman spectrum of Raman scattered light over a range of wavelengths denoted by $\lambda_{em}$.

The intensity of the Raman scattered light may also be enhanced as a result of two mechanisms associated with the Raman-active material. The first mechanism is an enhanced electromagnetic field produced at the surface of the Raman-active nanoparticles 116. As a result, conduction electrons in the metal surfaces of the nanoparticles 116 are excited into an extended surface excited electronic state called a "surface plasmon polariton" or "localized surface plasmon". Analytes adsorbed on or in close proximity to the nanoparticles 116 experience a relatively strong electromagnetic field. Molecular vibrational modes directed normal to the nanoparticle 116 surfaces are most strongly enhanced. The intensity of the surface plasmon polariton resonance depends on many factors, including the wavelengths of the Raman excitation light.

The second mode of enhancement, charge transfer, may occur as a result of the formation of a charge-transfer complex between the surfaces of the nanoparticles 116 and the analyte absorbed to the analyte particle surfaces. The electronic transitions of many charge transfer complexes are typically in the visible range of the electromagnetic spectrum.

Turning the incident angle of the Raman excitation light enables tuning the resonance. There are other ways to tune the resonance as well, such as by mechanical deformation of the grating, changing the geometry of the grating by applying E field on PZT material or by heating, changing the refractive index by electrical field (carrier injection or liquid crystal) or temperature.

The advantages of the Raman-active systems disclosed herein include compactness, uniform signal enhancement, and an integrated fluid channel with the features (either in close proximity or as the features themselves).

In the foregoing description, numerous details are set forth to provide an understanding of the present invention. However, it will be understood by those skilled in the art that the present invention may be practiced without these details. While the invention has been disclosed with respect to a limited number of embodiments, those skilled in the art will appreciate numerous modifications and variations therefrom. It is intended that the appended claims cover such modifications and variations as fall within the true spirit and scope of the invention.

What is claimed is:

1. A system for performing Raman spectroscopy comprising:
   a dielectric waveguide layer having two opposed ends and configured with at least one array of features, the at least one array of features comprising a subwavelength periodic array of lines, protrusions, or holes and being configured to provide guided-mode resonance for at least one wavelength of electromagnetic radiation, the combination of the dielectric waveguide layer and the at least one array of features forming a guided-mode resonance grating; and
   at least one fluid channel disposed in the waveguide layer for accepting a fluid containing an analyte, the fluid channel extending from one end of the waveguide layer to the other end and permitting flow of the fluid therethrough.

2. The system of claim 1 wherein the waveguide layer has a top surface and the at least one array of features providing the guided-mode resonance is disposed on the top surface, with the fluid channel disposed beneath the at least one array of features, the at least one array of features further comprising a lattice of approximately regularly spaced features protruding from the waveguide layer and formed from waveguide layer material.

3. The system of claim 2 wherein the lattice of approximately regularly spaced features further comprises either a one-dimensional lattice of features or a two-dimensional lattice of features.

4. The system of claim 1 wherein the waveguide has a featureless top surface and wherein a plurality of the fluid channels is disposed in the waveguide layer to form the at least one array of features and provide the guided-mode resonance, the at least one array of features further comprising a lattice of approximately regularly spaced features formed within the waveguide layer.

5. The system of claim 4 wherein the lattice of approximately regularly spaced features further comprises either a one-dimensional lattice of features or a two-dimensional lattice of features.

6. The system of claim 1 further including a material disposed on at least a portion of the inner surface of the at least one fluid channel, wherein the electromagnetic radiation produces enhanced Raman scattered light from analyte molecules located on or in proximity to the material.

7. The system of claim 6 wherein the material disposed on at least a portion of the inner surface of the at least one fluid channel comprises nanoparticles.

8. The system of claim 6 wherein the material disposed on at least a portion of the inner surface of the at least one fluid channel comprises a layer.

9. The system of claim 6 wherein the material disposed on at least a portion of the inner surface of the at least one fluid channel further comprises gold, silver, copper, or another suitable metal for forming surface plasmon polaritons when illuminated by the electromagnetic radiation.

10. The system of claim 1 wherein the waveguide layer is supported on a substrate.

11. An analyte sensor comprising:
an electromagnetic radiation source configured to emit a range of wavelengths of electromagnetic radiation;
a system for performing Raman spectroscopy comprising:
a dielectric waveguide layer having two opposed ends and configured with at least one array of features, the at least one array of features comprising a subwavelength periodic array of lines, protrusions, or holes and being configured to provide guided-mode resonance for at least one wavelength of electromagnetic radiation, the combination of the dielectric waveguide layer and the at least one array of features forming a guided-mode resonance grating; and
at least one fluid channel disposed in the waveguide layer for accepting a fluid containing an analyte, the fluid channel extending from one end of the waveguide layer to the other end and permitting flow of the fluid therethrough; and
at least one photodetector configured to detect Raman scattered light.

12. The sensor of claim 11 wherein the waveguide layer has a top surface and the at least one array of features providing the guided-mode resonance is disposed on the top surface, with the at least one fluid channel disposed beneath the at least one array of features, the at least one array of features further comprising a lattice of approximately regularly spaced features protruding from the waveguide layer and formed from waveguide layer material.

13. The sensor of claim 12 wherein the lattice of approximately regularly spaced features further comprises either a one-dimensional lattice of features or a two-dimensional lattice of features.

14. The sensor of claim 11 wherein the waveguide has a featureless top surface and wherein a plurality of the fluid channels is disposed in the waveguide layer to form the at least one array of features and provide the guided-mode resonance, the at least one array of features further comprising a lattice of approximately regularly spaced features formed within the waveguide layer.

15. The sensor of claim 14 wherein the lattice of approximately regularly spaced features further comprises either a one-dimensional lattice of features or a two-dimensional lattice of features.

16. The sensor of claim 11 further including a material disposed on at least a portion of the inner surface of the at least one fluid channel, wherein the electromagnetic radiation produces enhanced Raman scattered light from analyte molecules located on or in proximity to the material.

17. The sensor of claim 16 wherein the material disposed on at least a portion of the inner surface of the at least one fluid channel comprises nanoparticles.

18. The sensor of claim 16 wherein the material disposed on at least a portion of the inner surface of the at least one fluid channel comprises a layer.

19. The sensor of claim 16 wherein the material disposed on at least a portion of the inner surface of the at least one fluid channel further comprises gold, silver, copper, or another suitable metal for forming surface plasmon polaritons when illuminated by the electromagnetic radiation.

20. The sensor of claim 11 wherein the waveguide layer is supported on a substrate.

* * * * *